United States Patent [19]

Kamen

[11] Patent Number: 4,826,482
[45] Date of Patent: May 2, 1989

[54] ENHANCED PRESSURE MEASUREMENT FLOW CONTROL SYSTEM

[76] Inventor: Dean L. Kamen, 44 Gage Rd., Bedford, N.H. 03102

[21] Appl. No.: 92,481

[22] Filed: Sep. 3, 1987

Related U.S. Application Data

[63] Continuation-in-part of Ser. No. 22,167, Mar. 5, 1987, Continuation-in-part of Ser. No. 836,023, Mar. 4, 1986, Pat. No. 4,778,451.

[51] Int. Cl.$^4$ .............................................. A61M 5/00
[52] U.S. Cl. ...................................... 604/67; 604/246; 128/DIG. 13; 73/149
[58] Field of Search ................... 604/65, 67, 251, 253, 604/247, 246; 128/DIG. 12, DIG.13; 73/149

[56] References Cited

U.S. PATENT DOCUMENTS

| | | | |
|---|---|---|---|
| 2,116,636 | 5/1938 | Newman | 73/149 X |
| 2,747,400 | 5/1956 | Fatio | 73/149 |
| 4,486,190 | 12/1984 | Reinicke | 604/67 |
| 4,634,430 | 1/1987 | Polaschegg | 604/141 |

Primary Examiner—Stephen C. Pellegrino
Attorney, Agent, or Firm—Bruce D. Sunstein; Mary R. Jankousky; Paul C. Flattery

[57] ABSTRACT

The present invention provides a system for measuring flow of a fluid through a line. In the system, a region of fluid along the line is isolated from pressure effects outside of the region. A source region contains a measurement gas in communication with the isolated region, such that the source means and the isolated region together define a fixed volume, and such that a change in volume of fluid in the isolated region produces a complementary change in the volume of the source means with a resulting change in the pressure of the measurement gas contained in the source region. Further provided is a reservoir in communication with the source means for containing a known volume of measurement gas, and means for pumping measurement gas from the reservoir. The pressure of the measurement gas in the reservoir and the source region is monitored. This pressure data is then analyzed to determine the volume of fluid in the isolated region.

25 Claims, 2 Drawing Sheets

ENHANCED PRESSURE MEASUREMENT FLOW CONTROL SYSTEM

CROSS-REFERENCE TO RELATED APPLICATIONS

This is a continuation-in-part of application Ser. No. 022,167, filed on Mar. 5, 1987, and of application Ser. No. 836,023, filed on Mar. 4, 1986 now U.S. Pat. No. 4,778,451, both of which are incorporated herein by reference.

BACKGROUND OF THE INVENTION

1. Field of Invention

The present invention relates generally to systems for controlling fluid flow, and in particular to medical infusion technology, although other embodiments are discussed below.

2. Description of Related Art

The precise and accurate regulation of fluid flow is required in many settings. Precision and accuracy are particularly vital in medical infusion system, where there can be very narrow tolerances in infusion rates. For example, in chemotherapy, too slow an infusion rate may prove inefficacious, while too rapid a rate may prove toxic to the patient.

However, various elements inherent in medical infusion systems render problematic precise fluid delivery. One factor is the tubing that is used the deliver the fluid. Opening and closing of the line is typically accomplished by clamps, which can distort the walls of the tube leading to irregular flow rates. A second factor is that the patient receiving medication may move during infusion, producing varying fluid column heights, thereby affecting fluid flow. Third, the fact that fluid is delivered from a finite reservoir, such as an intravenous bag or bottle, that gradually empties, also affects the infusion rate.

Numerous approaches are known in the art to compensate for these factors. Certain prior art systems incorporate optical drop counting. Enhanced drop counting systems update drop count data with other measured quantities in order to compensate for varying drop size and splashing. Other approaches include bag weighing and pumping to regulate flow. However, systemic error is inevitable in most, if not all, of these arrangements.

SUMMARY OF THE INVENTION

The present invention provides a system for measuring flow of a fluid through a line. In the system, a region of fluid along the line is isolated from pressure effects outside of the region. A source chamber contains a measurement gas in communication with the isolated region, such that the source chamber and the isolated region together define a fixed volume, and such that a change in volume of fluid in the isolated region produces a complementary change in the volume of the source chamber with a resulting change in the pressure of the measurement gas contained in the source chamber. Further provided is a reservoir chamber in communication with the source chamber for containing a known volume of measurement gas, and means for pumping measurement gas from the reservoir chamber into the source chamber. The pressure of the measurement gas in the reservoir chamber and the pressure of the measurement fluid in the source chamber are monitored as fluid flows into and out of the region. This pressure data is then analyzed to determine the volume of fluid in the isolated region.

DESCRIPTION OF PREFERRED EMBODIMENTS

The present invention precisely measures discrete volume increments of fluid along a line by taking advantage of the known physical relationship between the pressure and volume of a gas. This is accomplished by isolating a region of the line and housing that region in communication with a measurement gas such that the isolated region of fluid and the measurement gas occupy a fixed and ascertainable volume. Thus, the movement of fluid into and out of the isolated region produces a corresponding change in the pressure of the measurement gas. The pressure of the measurement gas is monitored by a transducer, and the resulting data is used to compute the volume of fluid delivered, using methods described below.

In order to function properly, a system of this type must include calibration means for establishing reference quantities against which later measured quanitities can be compared. One approach to calibration is disclosed in two copending applications by the present inventor: Ser. No. 022,167, filed on Mar. 5, 1987, and Ser. No. 836,023 now U.S. Pat. No. 4,778,451, which are hereby incorporated by reference. The systems disclosed therein are calibrated by measuring the pressure of the measurement gas during a calibration cycle, during which the system, in the absence of fluid flow, induces a known decrease in volume of the measurement gas. The system then measures the pressure of the measurement gas during the flow of volume increments of fluid into and out of the isolated region. Using various disclosed physical and mathematical relationships, the system then computes the volume of fluid delivered using the calibration data together with pressure measurements taken during fluid flow.

Figure 3:
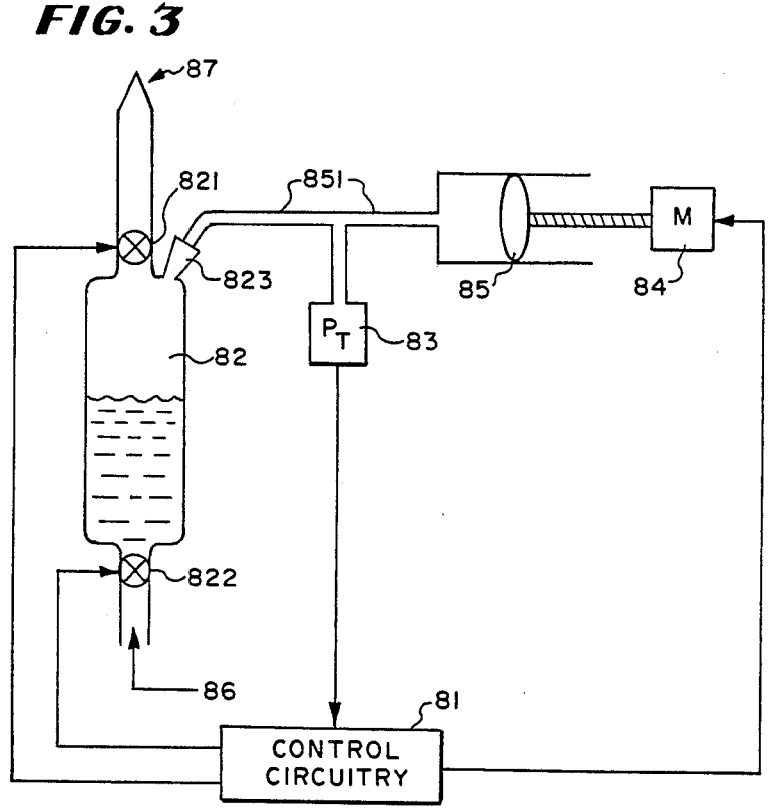
FIG. 3 shows a schematic drawing of the invention claimed in the parent case Ser. No. 836,023, filed Mar. 4, 1986 now U.S. Pat. No. 4,778,451.

FIG. 3 is a schematic representation of these systems. The embodiment shown in FIG. 3 uses a drip chamber as the isolated region. FIG. 3 shows the system having a drip chamber with an upper valve 821 and lower valve 822, which valves are operated by control circuitry 81. Pressure in the interior of the drip chamber 82 is monitored by transducer 83, which is also connected to control circuitry 81. The motor 84 drives piston 85 which compresses air in line 851. The motor 84 is also connected to control circuitry 81.

The earlier device proved to be extremely accurate at low rates of fluid delivery, but was not totally free from error. For example, a certain percentage of error was inherent in the mechanical creation of a precise volume displacement. In an embodiment employing a bellows arrangement to cause the volume displacement, error was found to be caused by a certain bowing out of the folds, which was found to be inevitable. Further, because moving parts are involved in expanding and contracting bellows, any precision could be affected by the aging of system. Other embodiments would still require precise mechanical displacements and generally good seal arrangement along the moving mechnical interface.

Another problem was found to exist in situation where the system is used to deliver relatively large volume increments of fluid, or where the volume increments are being dispensed into a line having significant back pressure. Where there is a significant amount of back pressure, relatively large volume displacements are necessary to produce the delivery of even small quantities of fluid.

The present device solves these problems of the earlier device by employing *pressure* displacement instead of the precise volume displacement of the earlier system. As will be described in greater detail below, the use of pressure displacement solves many of the problems of the earlier device. For example, unlike the volume displacement system, the use of pressure displacement, as described below, does not require a precise mechanical displacement, thus eliminating the errors associated therewith. Further, the system may utilize pressure displacement in such a fashion that the presence of back pressure does not necessitate significantly more pumping than would be the case in the absence of back pressure. Indeed, the system can be configured to compensate for a wide range of back pressures, including situations where back pressure exceeds fluid reservoir head pressure.

Figure 1:
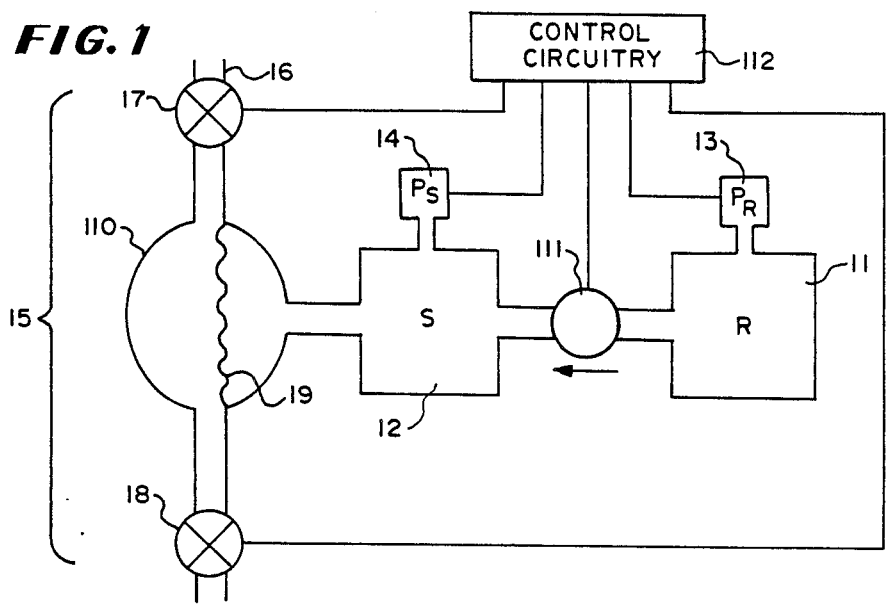
FIG. 1 shows a schematic drawing of a simplified embodiment of the present invention.

FIG. 1 shows a schematic drawing of a simplified embodiment of the present invention. The system includes two chambers, reservoir chamber 11 and source chamber 12 for housing a measurement gas. These chambers may be constructed of a rigid plastic using methods known in the art, although a wide variety of other materials, including metals, may also be suitable, the principal desideratum being that the chambers maintain a fixed volume regardless of the pressure of the measurement gas. It is thus contemplated that the volume of reservoir chamber 11 in this embodiment is known, although the volume could be determined heuristically in the course of initial calibration of the system. Each chamber has an associated pressure transducer 13, 14. The two chambers are connected, but are separated by a pump arrangement 111 that can move measurement gas contained in reservoir chamber 11 into source chamber 12 with a resulting decrease in pressure in the reservoir chamber and an increase in pressure in the source chamber. In this embodiment, the pump arrangement 111 also serves to prevent backflow of measurement gas. Thus, when the pump arrangment is activated, a pressure differential results between the two chambers which is maintained even after the pump arrangment ceases to pump.

The source chamber is in communication with a region 15 of the fluid line 16 that can be isolated by valves 17 and 18 from fluid pressure effects elsewhere in the line. Communication between the line fluid and the measurement gas is afforded through flexible membrane 19. A bulge 110 is provided in the region. The bulge serves two purposes. First, the bulge allows a greater amount of line fluid to impinge against the measurement gas, thus increasing the pressure communication between the line fluid and the measurement gas. Second, the bulge, because of its substantially spherical shape, provides maximum radial rigidity, thus preventing the isolated region from becoming distorted as a result of high measurement gas pressure.

Thus, it will be seen that when either valve 17 or valve 18 is closed, movement of fluid into or out of the isolated region 15 will, via flexible membrane 19, decrease or increase the volume of the measurement gas in the source chamber, with a resulting change in the pressure of the measurement gas.

For the reasons set forth below, the amount of fluid delivered can be determined by the relationship:

$$\Delta V_S = (\Delta P_R^o V_R / \Delta P_S^o)[\Delta P_S/(P_S + \Delta P_S)]$$

where:

$\Delta V_S$ = volume increment of fluid delivered $\Delta P_R^o$ = change in pressure of measurement gas in the reservoir chamber caused by movement of measurement gas from the reservoir chamber to the source chamber $V_R$ = volume of the reservoir chamber (known)

$\Delta P_S^o$ = change in pressure of measurement gas in the source chamber caused by movement of measurement gas from the reservoir chamber to the source chamber (measured before fluid flow)

$\Delta P_S$ = change in pressure of measurement gas in the source chamber resulting from movement of fluid out of the isolated region $P_S$ = pressure of the measurement gas in the source chamber This relationship is derived as follows:

First, assume that valves 17 and 18 are closed with fluid held in the isolated region. Initially, reservoir chamber 11 and source chamber 12 are each isolated. From Boyle's Law it is known that:

$$(1)\ P_S V_S = n_S R T$$

and $$(2)\ P_R V_R = n_R R T$$

where $V_S$ = the volume of the source chamber $n_S$ = the number of moles of measurement gas in the source chamber $P_R$ = the pressure [volume] of the reservoir chamber.

$n_R$ = the number of moles of measurement gas in the reservoir chamber

R = a constant

T = temperature of the measurement gas

Adding (1) and (2) yields $$(3)\ P_S V_S + P_R V_R = (n_S + n_R) R T$$

Because the source chamber and the reservoir chamber together comprise a closed system, $$(4)\ n_S + n_R = N$$

where N is a constant

Measurement gas is then moved from the reservoir chamber to the source chamber. This results in a change of the respective pressures of the two chambers. Because the chambers are rigid and because there is no fluid flow into or out of the isolated region, the respective volumes remain constant. Thus, $$(5a)\ (P_S V_S + P_R V_R) = [(n_S + n_R) R T]$$

which yields (5b) $(P_S + \Delta P_S^o)V_S + (P_R + \Delta P_R^o)V_R = NRT$

Subtracting (3) from (5) yields:

(6) $\Delta P_S^o V_s + \Delta P_R V_R = 0$

Solving for $V_S$ yields:

(7) $V_S = -\Delta P_R^o V_R / \Delta P_S^o$

At this point, the pump arrangment is then closed off, thus cutting off any communication between the two chambers. By Boyle's Law, it is known that at constant temperature, with respect to the source chamber volume:

(8) $P_S V_S = K_S$ $K_S$ = constant

Now valve 18 is opened, and fluid flows out of the isolated region. The outflow of fluid results in an increase in the volume of measurement gas housed in the source chamber, with a resulting decrease in pressure. By Boyle's Law it is known that the product of the measurement gas pressure in the source chamber volume and the source chamber volumes remain constant. Thus, (9) $(P_S + \Delta P_S)(V_S + \Delta V_S) = P_S V_S = K_S$ Solving equation (9) for $\Delta V_S$ yields (10a) $\Delta V_S = P_S V_S / (P_S + \Delta P_S) - V_S$ or (10b) $\Delta V_s = -\Delta P_s V_s / (P_s + \Delta P_s)$ Because we are assuming that some fluid has indeed flowed out of the isolated region, $P_S$ is not equal to the initial pressure $P_S^o$.

Using the relation of equation (7) to remove the $V_S$ term in equation (10) yields:

(11) $\Delta V_S = -[\Delta P_S/(P_S + \Delta P_S)][-\Delta P_R^o V_R/\Delta P_S^o]$ This equation can be rewritten as:

(12) $\Delta V_S = [\Delta P_R^o V_R/\Delta P_S^o][\Delta P_S/(P_S + \Delta P_S)]$ which is the final equation.

Total fluid delivered can be calculated by summing each individual $\Delta V_S$, which can be expressed by the following formula:

(13) $\sum_{i=1}^{x} \Delta V_S^j = \sum_{i=}^{x} [\Delta P_R^{oj} V_R/\Delta P_S^{oj}][\Delta P_S^j/(P_S^j + \Delta P_S^j)]$ The operation of the device depicted in FIG. 1 can be summarized by the following steps:

A. Initialize the system—valves 17 and 18 are closed with fluid held in the isolated region.

B. Measure the pressure of the measurement gas in the reservoir chamber and the source chamber.

C. Move some measurement gas from the reservoir chamber into the source chamber, and close off the source chamber from the reservoir chamber.

D. Measure the new pressures of the measurement gas in the reservoir chamber and the source chamber.

E. Open valve 18, which allows fluid to flow out of the isolated region 15.

F. Measure the pressure of the measurement gas in the source chamber, which is presumably decreasing as the volume increases in response to fluid leaving the isolated region.

G. Compute the volume of fluid delivered using equation (12).

It is contemplated that the data from the pressure transducers 13 and 14 will be interpreted by a microprocessor, or other computing unit, 112 which would also activate the pumping arrangment 15 and valves 17 and 18. It can be seen that the foregoing cycle is only exemplary, and that other cycles may be employed that can utilize the essential relationships described above. For example, steps E, F, and G may be repeated a desired number of times as a subcycle within larger cycle of steps B through G.

Figure 2:
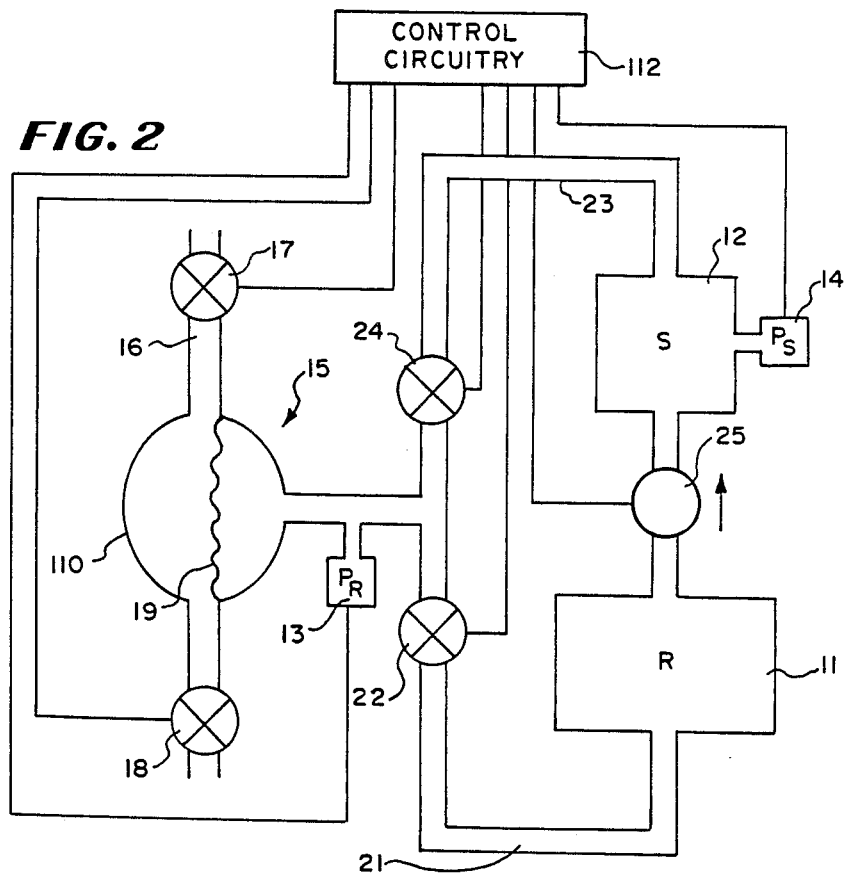
FIG. 2 shows a schematic drawing of a preferred embodiment of the present invention.

FIG. 2 shows a schematic diagram of a preferred embodiment of the present invention. This embodiment involves a slightly different arrangement for placing the reservoir chamber 11 and the source chamber 12 in communication with each other and with the isolated region of the fluid line. The embodiment of FIG. 2 provides a communication pathway 21, gated by valve 22, to the isolated region. The pathway 23 between the source chamber 12 and the isolated region 15 is gated by valve 24. In one mode of operation of this embodiment, it is possible to circulate measurement fluid around a closed circuit, namely from reservoir chamber 11 to source chamber 12 into the bulge 110 and then back to the reservoir chamber 11, with a resulting economy of operation.

In operation, assume, for example, that a measurement gas, such as air, is at one atmosphere in chambers 11 and 12, and that valves 17, 18, 22 and 24 are closed. Valves 17 and 22 are then opened. The opening of valve 17 allows fluid to flow into the isolated region. The opening of valve 22 defines two separate volumes. One of these volumes is the sum of the volumes of the reservoir chamber 11 and communication pathway 21 up to flexible membrane 19. The second is the volume of source chamber 12 plus the volume of that portion of communication pathway 23 up to valve 24. The pressures of measurement gas associated with these two volumes are then measured and recorded.

Valve 17 is then closed. Pump 25 is then run to create a pressure differential between the reservoir chamber and the source chamber. Then valve 22 is closed. At this point, because fluid flow has been stopped, the pressure of the measurement gas is the same on either side of valve 22, now closed. Thus, either pressure quantity could be measured. In the depicted embodiment transducer 13 measures the pressure between the valve and the flexible membrane.

The pressure $P_S$ of the source chamber up to valve 24, which is closed, and the pressure $P_{(R+D)}$ of the reservoir chamber, including communication pathway 21 up to flexible membrane 19, are measured before and after activation of pump 25 to calculate $\Delta P_S^o$ and $\Delta P_{(R+D)}^o$:

(14) $\Delta P_S^o = P_{Sf}^p - P_{Si}^p$

(15) $\Delta P_{(R+D)}^o = P_{(R+D)f}^p - P_{(R+D)i}^p$ $\Delta P_S^o$ = change in pressure of measurement gas in the source chamber resulting from activation of pump 25

$P_{Sf}^o$ = pressure of measurement gas in the source chamber after the activation of pump 25

$P_{Si}^o$ = pressure of measurement gas in the source chamber before the activation of pump 25

$\Delta P_{(R+D)}^o$ = change in pressure of measurement gas in the reservoir chamber (up to flexible membrane 19) resulting from activation of pump 25

$P_{(R+D)f}^o$ = pressure of measurement gas in the reservoir chamber (up to flexible membrane 19) after the activation of pump 25

$P_{(R+D)i}^o$ = pressure of measurement gas in the reservoir chamber (up to flexible membrane 19) before the activation of pump 25

From the Boyle's Law relationship, $$(16) \quad \Delta P_{(R+D)}^o V_{(R+D)} = -\Delta P_S^o V_S^o$$

$V_{(R+D)}^o$ = volume of reservoir chamber (up to flexible membrane 19) before fluid flow (this quantity changes because flexible membrane 19 moves in response to fluid flow into or out of the isolated region)

$V_S^o$ = volume of source chamber it is known that $$(17) \quad V_{(R+D)} = -\Delta P_S^o V_S^o / \Delta P_{(R+D)}^o$$

$V_{(R+D)}^\iota$ = *volume of reservoir chamber (up to flexible membrane 19) during fluid flow*

But, it is also known that $$(18) \quad V_D^o = V_{(R+D)}^o - V_R$$

$V_D^o$ = volume from valve 22 to flexible membrane 19
$V_R$ = known volume of the reservoir chamber so:

$$(19) \quad V_D^o = -\Delta P_S^o V_S^o / \Delta P_{(R+D)}^o - V_R$$

This volume $V_D$ can be checked by an alternative calculation. It will be seen that when valve 24 is opened, that the change in volume of fluid in the isolated region will be reflected in a change in pressure in the measurement gas in the source chamber up to the flexible membrane 19.

Thus, $P_{Si}$, which is the pressure of the source chamber before opening valve 24, is remeasured. If there has been no leak in the system, or other error, $P_{Si}$ should be equal to $P_{Sf}^o$, which was the pressure measured after activation of pump 25 but before fluid flow. Valve 24 is then opened. $P_{Scal}$, which is the resulting pressure of the measurement gas in the source chamber up to flexible membrane 19, is then measured and used to calculate $\Delta P_{Scal}$, the resulting change in pressure:

$$(20) \quad \Delta P_{Scal} = P_{Scal} - P_{Si}$$

Substituting source chamber values for reservoir chamber values in equate 19 yields the following equation:

$$(21) \quad V_D^o = \Delta P_{Scal}^o V_S^o / \Delta P_{(R+D)}^o - V_S$$

This $V_D^o$ should, if the system is operating properly, be equal to $V_D^o$ above. If the two values for $V_{Do}$ are not equal, this could indicate various system errors, including leakage of measurement gas.

After valve 24 has been opened, valve 18 is then opened to allow fluid flow. Valves 18 and 24 are then closed, and $P_{Sf}$ is measured. $\Delta P_S$ is calculated by subtracting $P_{Si}$ from $P_{Sf}$, and $\Delta V_S$ is calculated for the closed system $$(22) \quad P_{Si} V_{Si} = (P_{Si} + \Delta P_S)(V_{Si} + \Delta V_S)$$

by using the formula $$(23) \quad \Delta V_S = (P_{Si} V_{Si})/(P_{Si} + \Delta P_S) - V_{Si} = \Delta V_D$$

(because $V_S^o$ is a constant and $V_S = V_S + V_D$)

The operation of the device depicted in FIG. 2 and described above can be summed up in the following steps:

A. Initialize the system—measurement gas should be at one atmosphere in the reservoir and source chambers and valves 17, 18, 22 and 24 should be closed.

B. Measure the pressure of measurement gas in the reservoir chamber up to the flexible membrane 19, and the pressure of the measurement gas in the source chamber.

C. Open valves 17 and 22, allowing fluid to flow into the isolated region.

D. Close valve 17.

E. Activate pump 25 to create a pressure differential between the reservoir chamber and the source chamber, and then stop the pump.

F. Close valve 22.

G. Measure the new pressure of the source chamber, and the new pressure of either the reservoir chamber or the portion of communication pathway 21 between valve 22 and flexible membrane 19.

H. Calculate the volume of fluid in the isolated region using equations (14)—(21).

I. Open valve 24, and measure the pressure of the measurement gas in the source chamber.

J. Open valve 18, with resulting change in volume of fluid in the isolated region (normally outflow).

K. Close valves 18 and 24, and measure the resulting pressure of the measurement gas in the source chamber.

L. Calculate the volume of fluid delivered using equation (23).

It will be seen that measurement gas follows a cyclical travel pattern. Measurement gas is pumped from the reservoir chamber into the source chamber. The repeated opening and closing of valves 22 and 24 result in the migration of measurement gas from the source chamber back into the reservoir chamber. It will thus be seen that the system displays an innovative economy of design, since no venting or other means of pressure balancing is required.

Further, various modes of operation are possible. For example, the present invention can be configured to operate as a pump. There is a point in the operation cycle when valves 18 and 24 are both open. Because the measurement gas in source chamber 12 is at a relatively high pressure, fluid will tend to be pushed out of the isolated region. If a high enough pressure differential is created between the measurement gas in the source chamber and the measurement gas in the reservoir chamber, significant pumping action will result.

The pressure differential can also be used to solve the problem of back pressure. It will be seen that the system will provide data as to fluid flow through the line even if back pressure results in no flow at all, or in backflow. These phenomena will produce a corresponding change in measurement gas pressure, which in turn will yield a zero or negative volume increment using the calculations disclosed above. This information can be used to compensate for downstream pressure conditions. The microprocessor, or other controlling device, 112 can be programmed to increase the pressure differential where small or negative flows are detected. The pressure differential would be increased by activating pump 25 as needed.

It should also be noted that the detection of aberrant downstream line pressure conditions could also be used to detect infiltration, or other undesirable conditions, all in a manner similar to that disclosed in my copending U.S. application Ser. No. 021,294, filed Mar. 3, 1987, which is hereby incorporated by reference. Similarly, the approaches described in my U.S. application Ser. No. 022,167, filed Mar. 5, 1987, can be used to determine when an upstream reservoir is reaching a near empty condition, to detect the presence of air in the fluid line, and to purge air from the fluid line.

As in the case of FIG. 1 above, the foregoing cycle is only exemplary and other cycles may be employed that can utilize the essential relationships described above. Thus, for example, steps J through L may be repeated a desired number of times as a subcycle within a larger cycle of steps B through L. Furthermore, if the operating pressure of source chamber 12, is kept at approximately that of the line pressure at valve 17, the system may be operated in a controller mode.

It is contemplated to construct the embodiment of FIG. 2 out of rigid plastic, arranging the chambers and pathways in such a way that the final structure can be housed in a block configuration, although other materials, including metal, and configurations, known to practitioners of ordinary skill in the art, are also be within the spirit of the present invention.

What is claimed is:

1. A system for controlling flow of a fluid through a line, the system comprising:
    dispensing means (i) for isolating a region of the fluid in the line from effects of pressure in the line outside of the region, the region having an input and an output for the first fluid, and (ii) for repetitively dispensing into and out of the region volume increments of the fluid;
    source means for containing a measurement gas in communication with the isolated region, such that the source means and the isolated region together define a fixed volume, and such that a change in volume of the fluid in the isolated region produces a complementary change in the volume of the source means with a resulting change in the pressure of the measurement gas contained in the source means;
    reservoir means in communication with the source means for containing a known volume of measurement gas;
    pumping means for moving a quantity of measurement gas between the reservoir means and the source means, thereby producing changes in the pressure of the measurement gas contained in the reservoir means and the measurement gas contained in the source means;
    pressure monitoring means for generating data relating to the pressure of the measurement gas in the source means and the measurement gas in the reservoir means; and
    control means, in communication with the pressure monitoring means, the pumping means, and the dispensing means, for causing the dispensing means to dispense first fluid in determinable increments based on data from the pressure monitoring means taken at predetermined points during a calibration and dispensing cycle.

2. A system according to claim 1, wherein the measurement gas is air.

3. A system according to claim 1, wherein the dispensing means includes an input valve at the fluid input to the region and an output valve at the fluid output from the region.

4. A system according to claim 3, wherein the isolated region includes a flexible interface surface defining a boundary between the fluid and the measurement gas contained in the source means.

5. A system according to claim 4, wherein the isolated region includes a rigid enclosure with an input, an output, and a window, the flexible interface surface covering the window.

6. A system according to claim 3, wherein the control means includes means for controlling first fluid flow in accordance with a calibration and dispensing cycle as follows:
    (A) closing the input and output valves with fluid in present in the isolated region;
    (B) measuring the pressure in the reservoir means and the source means;
    (C) actuating the pumping means to move measurement gas from the reservoir means to the source means;
    (D) measuring the resulting pressure in the reservoir means and the source means;
    (E) closing off the pumping means, such that any communication between the reservoir means and the source means is cut off;
    (F) opening the output valve, thereby allowing fluid to flow out of the isolated region;
    (G) measuring the resulting change in pressure of the measurement gas contained in the source means;
    (H) calculating the volume of fluid delivered based on data from steps (B), (D) and (G);
    (I) closing the output valve;
    (J) opening the input valve, thereby allowing fluid to flow into the isolated region;
    (K) closing the input valve;
    (L) repeating subcycle (F)-(K) until a desired amount of fluid has been delivered.

7. A system according to claim 6 further including in the calibration and dispensing cycle:
    (M) monitoring the rate of fluid delivery, and if the rate of fluid delivery has dropped below a desired level, increasing the pressure difference between the reservoir means and the source means, and resuming the cycle from step (D).

8. A system for controlling flow of a fluid through a line, the system comprising:
    dispensing means (i) for isolating a region the first fluid in the line from effects of pressure in the line outside of the region, the region having an input and an output for the first fluid, and (ii) for repetitively dispensing into and out of the region volume increments of the fluid;
    source means for containing a first volume of measurement gas;
    reservoir means in communication with the source means for containing a second volume of measurement gas;
    pumping means for moving a quantity of measurement gas between the reservoir means and the source means, thereby producing changes in the pressure of the measurement gas in the reservoir means and in the pressure of the measurement gas contained in the source means;

a source communication pathway between the source chamber and the isolated region and a reservoir communication pathway between the reservoir chamber and the isolated region, the source communication pathway and the reservoir communication pathway joining to at some point along each respective pathway to form a joint communication pathway leading to the isolated region;

source valving means for opening and closing the source communication pathway;

reservoir valving means for opening and closing the reservoir communication pathway;

the isolated region, the source means and the reservoir means, and the source communication pathway, the reservoir communication pathway and the joint communication pathway being so disposed in relationship with each other such that they together define a fixed volume, and such that a change in volume of the fluid in the isolated region produces a correlative change in the joint communication pathway and in any other enclosure in pressure communication with the joint communication pathway;

pressure transducing means (i) in pressure communication with the source means for generating data relating to the pressure of the measurement gas in the source means, and in any other enclosure in pressure communication with the source means and (ii) in pressure communication with the joint communication pathway for generating data relating to the pressure of the measurement gas in the joint communication pathway, and in any other enclosure in pressure communication with the joint communication pathway; and control means, in communication with the pressure monitoring means, the pumping means, the dispensing means, the source valving means, and the reservoir valving means, for causing the dispensing means to dispense first fluid in determinable increments based on data from the pressure monitoring means taken at predetermined points during a calibration and dispensing cycle.

9. A system according to claim 8, wherein the measurement gas is air.

10. A system according to claim 8, wherein the dispensing means includes an input valve at the fluid input to the region and an output valve at the fluid output from the region.

11. A system according to claim 10, wherein the isolated region includes a flexible interface surface defining a boundary between the fluid and the measurement gas contained in the source means.

12. A system according to claim 11, wherein the isolated region includes a rigid enclosure with an input, an output, and a window, the flexible interface surface covering the window.

13. A system according to claim 10, wherein the control means includes means for controlling first fluid flow in accordance with a pumping cycle as follows:

(A) initializing the system by establishing a pressure of one atmosphere of the measurement gas in the reservoir means, the source means, and all of the communication pathways, and closing the input valve, the output valve, the source valve, and the reservoir valve;

(B) taking pressure readings at the pressure transducer means;

(C) opening the input valve and the reservoir valve, thereby allowing fluid to flow into the isolated region;

(D) actuating the pumping means to create a pressure differential between the reservoir means and the source means, and then stopping the pump;

(E) closing the fluid input valve and the reservoir valve;

(F) taking a new pressure reading at the pressure transducer means;

(G) calculating the volume of fluid in the isolated region based on the data obtained in steps (B) and (F);

(H) opening the source valve;

(I) taking a pressure reading at the pressure transducer of the pressure of the measurement gas in the source means;

(J) opening the fluid output valve, thereby causing a change in the volume of fluid in the isolated region;

(K) closing the fluid output valve and the source valve, and measuring taking a pressure reading at the pressure transducer means of the pressure of the measurement gas in the source means;

(L) calcuting the volume of fluid delivered using data obtained from (G), (I), and (K);

(M) repeating steps (F)-(L) until a desired volume of fluid has been delivered.

14. A system according to claim 13 further including in the dispensing cycle:

monitoring the rate of fluid delivery, and if the rate of fluid delivery has dropped below a desired level, increasing the pressure difference between the reservoir means and the source means, and resuming the cycle from step (E).

15. A method for controlling flow of a fluid through a line, the method comprising the following steps:

(i) providing in the line a region that can be selectably isolated from effects of pressure in the line outside of the region;

(ii) housing a source volume of measurement gas in communication with the region such that the region and the source volume occupy a fixed volume, such that a change of volume of fluid in the region produces a complementary change in the volume of the source volume, with a resulting change in the pressure in the source volume;

(iii) housing a constant reservoir volume of measurement gas in communication with the source volume, such that moving a quantity of measurement gas between the reservoir volume and the source volume produces corresponding changes in the pressure in the source volume and in the reservoir volume;

(v) providing means for generating on a continual basis data relating to the pressure in the source volume and in the reservoir volume; and (vi) causing fluid to be dispensed through the line in determinable increments based on pressure data generated at predetermined points during a calibration and dispensing cycle.

16. A method according to claim 15, wherein the calibration and dispensing cycle includes the following:

(A) isolating some quantity of the fluid in the region from effects of pressure in the line outside of the isolated region;

(B) measuring the pressure in the reservoir volume and in the source volume;

(C) moving a quantity of measurement gas between the reservoir volume and the source volume;

(D) measuring the new pressure in the source volume and in the reservoir volume;

(E) changing the volume of fluid in the region;

(F) isolating the fluid in the region from effects of pressure in the line outside of the region;

(G) measuring the resulting pressure in the source volume; and (H) calculating the change in volume of fluid in the region based on the pressure measurements.

17. A method according to claim 16, wherein: step (A) includes allowing a volume increment of fluid to flow into the region and then isolating the volume increment from effects of pressure in the line outside of the isolated region; step (C) includes moving the measurement gas from the reservoir volume to the source volume; and step (E) includes allowing some fluid to flow out of the region.

18. A method according to claim 17, including the additional steps of:

(I) allowing a volume increment of the fluid to flow into the region;

(J) isolating the fluid in the isolated region from effects of pressure in the line outside of the isolated region; and (K) measuring the pressure of the measurement gas in the source volume;

(L) repeating steps (E) through (K) until a desired amount of fluid has been delivered.

19. A method according to claim 17, including the additional steps of:

(I) pumping a quantity of measurement gas from the source volume to the reservoir volume;

(J) repeating steps (A) through (I) until a desired amount of fluid has been delivered.

20. A method for controlling flow of fluid through a line the method comprising:

(i) providing in the line a region that can be selectably isolated from effects of pressure in the line outside of the region;

(ii) housing a common volume of measurement gas in communication with the region;

(iii) housing a source volume of measurement gas that can be selectably put in communication with the common volume such that the region, the common volume and the source volume together define a fixed volume, such that a change of volume of fluid in the region produces a complementary change in the volume of the common volume with a resulting change in the pressure of the measurement gas in the source volume;

(iv) housing a reservoir volume of measurement gas that can be selectably put in communication with the common volume such that the region, the common volume and the reservoir volume together define a fixed volume, such that a change of volume of fluid in the region produces a complementary change in the volume of the common volume with a resulting change in the pressure of the measurement gas in the reservoir volume;

(v) providing a means for moving a quantity of measurement gas between the reservoir volume and the source volume, thereby producing changes in the pressure in the source volume and in the reservoir volume;

(vi) providing means for generating on a continual basis data relating to the pressure of in the source volume and in the reservoir volume; and (vii) causing fluid to be dispensed through the line in determinable increments based on pressure data generated at predetermined points during a calibration and dispensing cycle.

21. A method according to claim 20, wherein the calibration and dispensing cycle includes the following steps:

(A) measuring the pressure in the common volume, the reservoir volume and the source volume, shutting off communication between the source volume and the common volume, and opening communication between the common volume and the reservoir volume;

(B) opening communication between the region and the line whereby fluid may flow into or out of the isolated region;

(C) isolating the fluid in the region from effects of pressure in the line outside of the region, and moving a quantity of measurement gas between the reservoir volume and the source volume;

(D) measuring the pressure in the source volume, and measuring the pressure in the reservoir volume, shutting off communication between the common volume and the reservoir volume, and calculating based on pressure measurements taken the volume of fluid which has entered or left the region in step (B);

(E) opening communication between the region and the source volume;

(F) measuring the pressure in the source volume;

(G) opening communication between the region and the line whereby fluid may flow into or out of the region;

(H) isolating the fluid in the region from effects of pressure in the line outside of the isolated region;

(I) measuring the pressure in the source volume; and (J) calculating based on pressure measurements the volume of fluid which has entered or left the region in step (G).

22. An improved system for controlling the flow of fluid through a line of the type including a region in the line that can be selectably isolated from pressure effects in the line outside of the region by microprocessor-controlled input and output valves, wherein the improvement comprises:

source means for containing a variable volume of measurement gas in communication with the region, such that the source means and the region, when isolated, together define a fixed volume, and such that a change in volume of the fluid in the region produces a complementary change in the volume of the measurement gas in the source means with a resulting change in the pressure in the source means;

reservoir means in communication with the source means for containing a fixed volume of measurement gas;

pumping means for moving a quantity of measurement gas between the reservoir means and the source means; and pressure monitoring means for generating source means measurement gas pressure data and reservoir means measurement gas pressure data during a calibration and dispensing cycle.

23. An improved system according to claim 22, wherein the calibration and dispensing cycle is as follows:
   (A) closing the input and output valves with some amount of the fluid present in the isolated region;
   (B) measuring the pressure in the reservoir means and the source means;
   (C) actuating the pumping means to move measurement gas from the reservoir means to the source means;
   (D) shutting off the pumping means;
   (E) measuring the resulting pressure in the reservoir means and the source means;
   (F) opening the output valve, whereby fluid is allowed to flow out of the isolated region;
   (G) closing the output valve;
   (H) measuring the resulting pressure in the source means; and
   (I) calculating the volume of fluid delivered based on the pressure data.

24. An improved system for controlling the flow of fluid through a line of the type including a region in the line that can be selectably isolated from pressure effects in the line outside of the region by microprocessor-controlled input and output valves, wherein the improvement comprises:
   common means for containing a variable volume of measurement gas in communication with the region, such that the common volume and the region, when isolated, together define a fixed volume, such that a change in the volume of the fluid in the region produces a complementary change in the volume of the measurement gas in the common volume with a resulting change in the pressure in the common means;
   source means for containing a known volume of measurement gas;
   reservoir means for containing a known volume of measurement gas;
   pumping means for moving a quantity of measurement gas between the reservoir means and the source means;
   source valving means for selectably permitting communication between the common means and the source means;
   reservoir valving means for selectably permitting communication between the common means and the reservoir means; and
   pressure monitoring means for generating source means measurement gas pressure data and reservoir means measurement gas pressure data during a calibration and dispensing cycle.

25. An improved system according to claim 24, wherein the calibration and dispensing cycle is as follows:
   (A) closing the input valve, the source valving means and the output valve, opening the reservoir valving means, and measuring the pressure in the common means, the reservoir means and the source means;
   (B) opening the input valve, and turning on the pumping means to move a quantity of measurement gas from the reservoir means to the source means;
   (C) turning off the pumping means, and closing the input valve;
   (D) measuring the pressure in the source means and the reservoir means, closing the reservoir valving means and calculating based on pressure measurements the volume of fluid which has entered or left the isolated region between steps (B) and (C);
   (E) opening the source valving means;
   (F) measuring the pressure in the source means;
   (G) opening the output valve;
   (H) closing the output valve;
   (I) measuring the pressure in the source means;
   (J) calculating based on pressure measurements the volume of fluid which has left or entered the region between steps (G) and (H).

* * * * *